US008887557B2

(12) United States Patent
Chawla et al.

(10) Patent No.: US 8,887,557 B2
(45) Date of Patent: Nov. 18, 2014

(54) FRACTIONATION OF DE-ASPHALTED OIL OF VACUUM RESID USING PREPARATIVE HIGH PERFORMANCE LIQUID CHROMATOGRAPHIC SEPARATIONS

(75) Inventors: Birbal Chawla, Cherry Hill, NJ (US); Bryan E. Hagee, Glassboro, NJ (US); Larry A. Green, Mickleton, NJ (US); Frank P. Di Sanzo, Cherry Hill, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 277 days.

(21) Appl. No.: 13/223,739

(22) Filed: Sep. 1, 2011

(65) Prior Publication Data
US 2013/0055795 A1    Mar. 7, 2013

(51) Int. Cl.
| | |
|---|---|
| *G01N 30/02* | (2006.01) |
| *G01N 30/88* | (2006.01) |
| *B01D 15/36* | (2006.01) |
| *B01D 15/34* | (2006.01) |
| *B01D 15/18* | (2006.01) |
| *G01N 30/46* | (2006.01) |

(52) U.S. Cl.
CPC .............. *G01N 30/88* (2013.01); *G01N 30/461* (2013.01); *G01N 30/468* (2013.01); *G01N 2030/8854* (2013.01); *B01D 15/362* (2013.01); *B01D 15/34* (2013.01); *B01D 15/1871* (2013.01)
USPC ......... 73/61.53; 210/660; 422/68.1; 436/161; 436/139

(58) Field of Classification Search
USPC ....................... 73/61.52, 61.53; 436/161, 139; 210/660; 422/68.1
See application file for complete search history.

(56) References Cited

U.S. PATENT DOCUMENTS

| | | | | |
|---|---|---|---|---|
| 4,826,603 | A | * | 5/1989 | Hayes et al. .................. 210/635 |
| 5,411,658 | A | * | 5/1995 | Chawla et al. .................. 208/89 |

(Continued)

FOREIGN PATENT DOCUMENTS

WO    2010114587 A1    10/2010

OTHER PUBLICATIONS

Snyder, "Routine Determination of Aromatic Hydrocarbon Types in Catalytically Cracked Gas Oils by Linear Elution Adsorption Chromatography", Analytical Chemistry, vol. 36, No. 4, pp. 774-781 (Apr. 1964).

(Continued)

*Primary Examiner* — Hezron E Williams
*Assistant Examiner* — Hoang Nguyen
(74) *Attorney, Agent, or Firm* — Ronald D. Hantman; Glenn T. Barrett; Andrew T. Ward

(57) ABSTRACT

Two quantitative separation approaches to fractionate de-asphalted oils (DAOs) into seven classes of compounds (saturates, 1-4$^+$ ring-aromatics, sulfides, and polars). In the first step (named as "SGS") of present invention, the DAO of a petroleum vacuum resid is separated in to four classes of compounds, namely saturates, aromatics, and sulfides. In this first step of separation, about 3 grams of a DAO can be separated. Whereas in the second step (named as "ARC" separation) of invention, only less than 300 mg of the aromatic fraction obtained in "SGS" (described above) can be further fractionated at very low temperature (about −40 degrees centigrade) into 4 fractions, namely 1-ring, 2-ring, 3-ring, and 4$^+$-ring aromatics. The present invention protocol is suitable for a wide range of compositionally different DAOs of petroleum vacuum resids.

11 Claims, 2 Drawing Sheets

A Schematic Diagram of Silica Gel Separation Technique Steps

(56) References Cited

U.S. PATENT DOCUMENTS

| | | | |
|---|---|---|---|
| 7,598,487 B2* | 10/2009 | Qian et al. | 250/282 |
| 8,114,678 B2* | 2/2012 | Chawla et al. | 436/161 |
| 2010/0218585 A1* | 9/2010 | Chawla et al. | 73/1.02 |

OTHER PUBLICATIONS

Suatoni et al., Preparative Hydrocarbon Compound Type Analysis by High Performance Liquid Chromatography, Journal of Chromatographic Science, vol. 14, pp. 535-537 (Nov. 1976).

Altgelt, et al., "Composition and Analysis of Heavy Petroleum Fractions", Chemical Industries, vol. 54, pp. 241-255.

Lundanes et al., Quantitation of High Boiling Fractions of North Sea Oil After Class Separation and Gel Permeation Chromatography, Journal of Liquid Chromatography, vol. 8, No. 6, pp. 1035-1051 (1985).

Carbognani et al., "Preparative Compound Class Separation of Heavy Oil Vacuum Residua by High Performance Liquid Chromatography", Fuel Science and Technology International, vol. 8, No. 1, pp. 1-15 (1990).

Guadalupe et al., "Isolation of Sulfides in Oils", Organic Geochemistry, vol. 17, No. 3, pp. 355-361 (1991).

Orr, "Separation of Alkyl Sulfides by Liquid-Liquid Chromotography on Stationary Phases Containing Mercuric Acetate", Analytical Chemistry, vol. 38, No. 11, pp. 1558-1562, (Oct. 1966).

Haines et al., "Separating and Characterizing High-Boiling Petroleum Distillates: The USBM-API Procedure", U.S. Energy Research & Development Administration, Office of Public Affairs, Technical Information Center, pp. 1-30, (Jul. 1975).

Hayes et al., The Analysis of Hydrocarbon Distillates for Group Types Using HPLC With Dielectric Constant Detection: A Review, Journal of Chromatographic Science, vol. 26, pp. 210-217, (May 1988).

DiSanzo et al., Determination of Total Aromatic Hydrocarbons in Lube Base Stocks by Liquid Chromotagrphy With Novel Thermospray Flame Ionization Detection, Analytical Chemistry, vol. 65, pp. 3359-3362 (1993).

PCT International Search Report issued Nov. 20, 2012 in corresponding PCT Application No. PCT/US2012/053285, 5 pgs.

PCT Written Opinion issued Nov. 20, 2012 in corresponding PCT Application No. PCT/US2012/053285, 8 pgs.

Padlo et al., "Hydrocarbon Class Analysis of Coal-Derived Liquids Using High Performance Liquid Chromatography", Fuel Processing Technology, vol. 49, No. 1-3, (1996), pp. 247-258.

Ghosh et al., "Prediction of Chromatographic Retention Times for Aromatic Hydrocarbons", Energy & Fuels, vol. 20, No. 2, (2006), pp. 609-619.

Peramanu et al., "Molecular Weight and Specific Gravity Distributions for Athabasca and Cold Lake Bitumens and their Saturate, Aromatic, Resin, and Asphaltene Fractions", Industrial & Engineering Chemistry Research, vol. 38, No. 8, (1999), pp. 3121-3130.

* cited by examiner

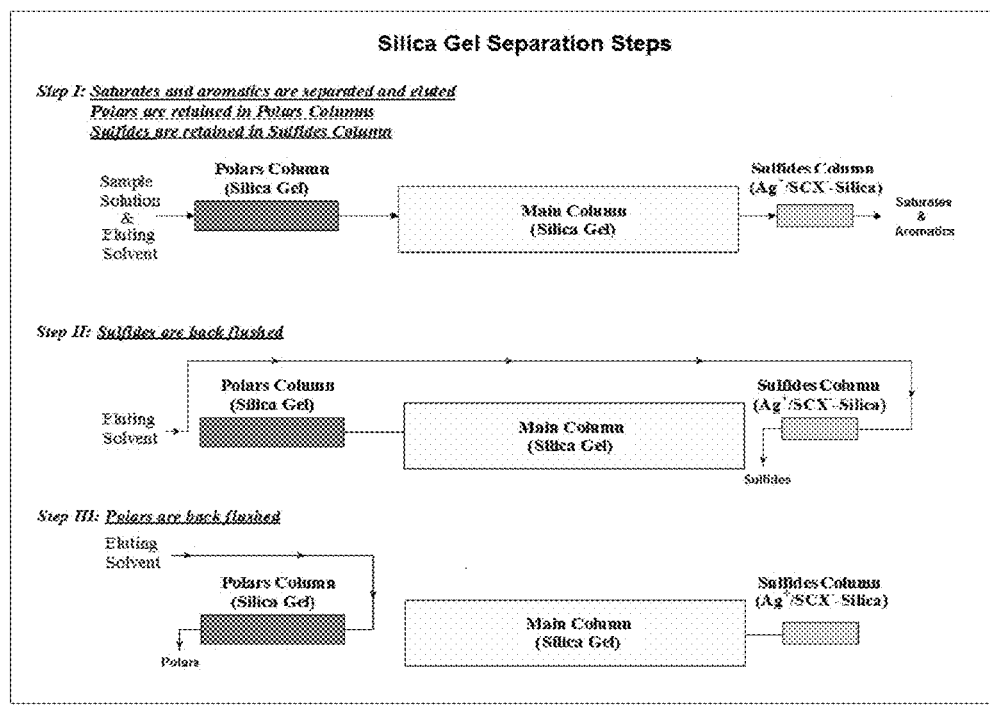
Figure 1: A Schematic Diagram of Silica Gel Separation Technique Steps

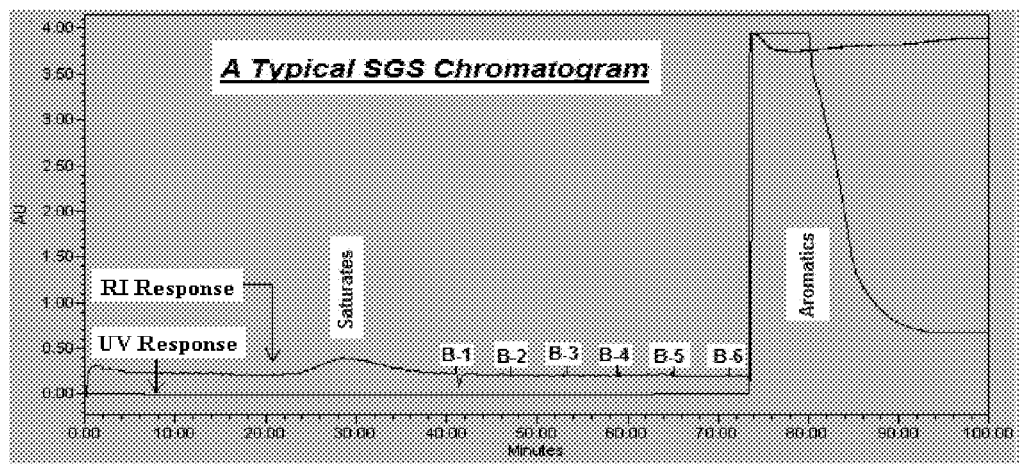
Figure 2: A Typical Separation Chromatogram for the De-asphalted Oil.
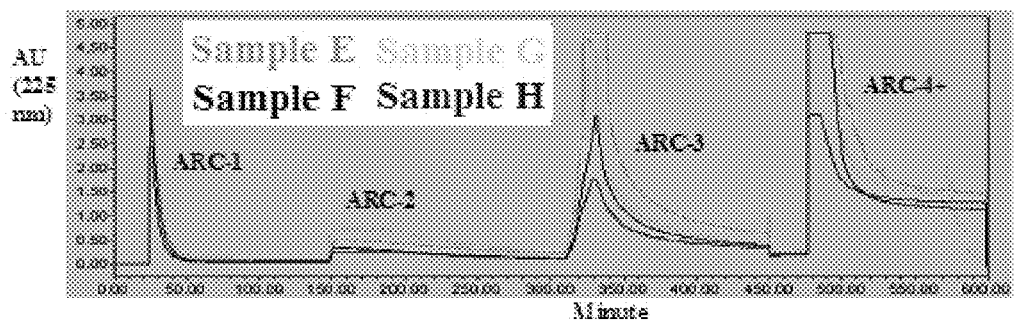
Figure 3: Typical Separation Chromatograms of 4 Compositionally Different Aromatics Fractionations.

FRACTIONATION OF DE-ASPHALTED OIL OF VACUUM RESID USING PREPARATIVE HIGH PERFORMANCE LIQUID CHROMATOGRAPHIC SEPARATIONS

BACKGROUND OF THE INVENTION

The present invention is a method for the fractionation of de-asphalted oil of vacuum resid using preparative High Performance Liquid Chromatographic (HPLC) separations.

The petroleum vacuum resid de-asphalted oils (DAOs), boiling above ~1000° F., are too complex to be analyzed as such for detailed compositional information even with the most modern analytical techniques/instruments. It is, therefore, essential to fractionate them into several sub-fractions so that the detailed/extensive compositional analyses can be performed using high resolution mass spectrometry and other analytical techniques.

Extensive documentation exists in the literature for the class separation of hydrocarbons and heteroatoms, such as nitrogen, oxygen and sulfur containing petroleum compounds in various petroleum streams (1-5). Silica gel or alumina have been the most common substrates for the LC fractionation of heavy petroleum streams in to total saturates (paraffins plus cycloparaffins also called naphthenes), total aromatics and total polars. In some cases, amino and/or cyano functional groups bonded to silica gel have been used for similar saturates, aromatics and polars separations.

The separation of sulfur compounds, such as sulfides, is more difficult to accomplish with conventional LC substrates. Because of the unique interaction of sulfides with certain metallic ions, ligand exchange chromatography has been documented. The most common metallic ions used have included silver (6), palladium (3), mercury (7) and copper (8). In general, these metallic ions are deposited from their salts onto substrates like silica gel (6) or week-ion exchange substrates (8). To the best of our knowledge, the use of strong-ion exchange substrate such as alkyl- or aryl-sulfonic functional groups bonded to silica gel and containing silver ions for the isolation of sulfides has not been documented in the literature.

The use of ligand exchange with sulfonic functional groups containing silver ions has been demonstrated for the separation of total aromatics from total saturates (9, 10) for lube basestocks. The advantage of such substrate for total saturates and total aromatics is the enhanced separation imparted by the silver ion.

The separation of aromatics into subclasses consisting of mono-, di-, tri- and or tetra+ aromatic rings separations are best accomplished using several solid supports e.g. silica gel, bonded amino (3), amino-cyano (3) and dinitroanilinopropyl (DNAP) (3). The advantage of using bonded substrates is that the separation column(s) are re-useable for many separations.

The complexity of aromatic hydrocarbons types increases significantly with increasing molecular weight and/or boiling point of the petroleum fractions. As a result, the separation of the aromatic group into individual ring numbers (i.e. mono-, di- etc) is challenging as compound class overlap may occur, particularly with sterically hindering alkylgroups substituted on the individual aromatic rings. In addition, the presence of saturated cyclic rings on the aromatic rings may lead to longer retention on the column substrates and overlap with the next aromatic ring class. To enhance the resolution among the aromatic ring classes of compounds, cryogenic HPLC separation at temperatures of <0° C. are more effective. The current literature is void in such low temperature operating conditions when applied to the separation of heavy petroleum fractions.

The present invention presents a relatively efficient separation scheme for heavy petroleum fractions. It combined in a single step a separation of total saturates, total aromatics, polars and sulfides. A second offline separation fractionates the total aromatics from the first step into aromatic rings using a cryogenic separation at temperatures substantially lower than 0° C. The cryogenic separation enhances the resolution among the aromatics rings.

SUMMARY OF THE INVENTION

The present invention supports the development of the molecule-based models for processing and upgrading of heavy petroleum streams using two preparative High Performance Liquid Chromatographic (HPLC) separation techniques for fractionation of the de-asphalted oils of vacuum resids. Both of the separation techniques were developed using the DAOs extracted from vacuum resids (VR) using n-heptane solvent.

The first HPLC separation technique, named 'SGS' (Silica Gel Separation), where a DAO is fractionated into four classes of compounds: 'saturates', 'aromatics', 'sulfides', and 'polars'. This technique utilizes two silica gel packed stainless steel columns (laboratory-packed) and a commercially prepared silver nitrate loaded strong-cation-exchange (Ag+/SCX-silica gel) column. Compared to relatively low boiling petroleum molecules (boiling below ~1000° F.), the larger molecule size, lower solubility, and different adsorption characteristics of the DAO molecules made the separations more difficult. Sample loading, eluting solvent volume and the solvent polarity were optimized so that the total mass recovery was close to 100% and the overlaps between the separated fractions were as minimal as chromatographically possible. It was determined that the amount of sample loading is a critical parameter for an effective separation between saturates and aromatics. At present, for optimum separations, about 3 grams of the sample can be fractionated in a typical silica gel separation (sample: SG ratio=1:250).

The second separation technique, named 'ARC' (Aromatic Ring Class) where a portion of 'Aromatics' (recovered in SGS-first separation technique) is further separated into Ring-1, Ring-2, Ring-3, and Ring4+ aromatics (aromatic hydrocarbons plus thiophenic compounds). This technique utilizes a packed with [3-(2,4-dinitroanilino-)propyl]-silica gel (DNAP-silica or DNAP) column. The ARC technique is operated at a sub-ambient temperature (approx. −40° C.). In order to obtain good chromatographic separation, only about 200 mg of aromatics (sample: adsorbent ratio=1:600) can be fractionated at a time. All of the ARC separated fractions are analyzed using proton-NMR to establish the purity of each fraction.

BRIEF DESCRIPTION OF THE DRAWINGS

FIG. 1 shows schematic diagram of the silica gel separation column of the first step of the invention.

FIG. 2 shows a typical separation chromatogram analysis of the separation of the de-asphalted oil.

FIG. 3 shows a typical separation chromatogram analysis an aromatics fractionation.

DESCRIPTION OF THE PREFERRED EMBODIMENT

The present invention supports the development of the molecular-based models for processing and upgrading of heavy petroleum streams (BP>~1000° F.), using two High Performance Liquid Chromatographic (HPLC) separation techniques for fractionation of the de-asphalted oils of vacuum resids. Both of the separation techniques were developed using the DAOs extracted from vacuum resids (VR) using n-heptane solvent. These two separation techniques are discussed below.

I. Silica Gel Separation (SGS) Technique

An automated preparative high performance liquid chromatographic (HPLC) separation technique has been developed to separate the DAO into four classes of compounds: 'saturates', 'aromatics', 'sulfides', and 'polars'. Three columns: polars-column, main-column, and sulfides-column, were used in series. Details are given below and under HPLC Operational Procedure section.

It was determined that the level of sample loading was a critical parameter for an effective separation between saturates and aromatics. At present, for optimum separations, about 3 grams of the sample can be used in a typical silica gel separation (sample: SG ratio=1:250).

The HPLC system is equipped with a Waters quaternary solvent delivery pump and a dual wavelength UV detector. The solvent delivery pump can be programmed to deliver either one of the four different solvents or their mixtures in the desired ratios for the specific duration at a selected rate of up to 40 mL/min. The refractive index detector (Shodex RI-72), which can handle high solvent flow rate, was purchased from J. M. Science Inc. (New York).

Four switching valves (three 6-port and one 4-port) are used in order to have the options of back-flushing both of the 'sulfides' and 'polars' columns independently. One 6-port switching valve was converted to be used as an injector. Two large volume injection loops were installed to accommodate up to 80 ml of the DAO solution in cyclohexane. A 12-port fraction-collecting valve was converted to collect all of the necessary fractions generated in a separation. All these valves were purchased with ⅛-inch fittings from VICI Valco Instruments.

The operation of the HPLC system is controlled by the Waters Millennium chromatographic management system.

The main column (1000×30 mm) and the polars column (500×21 mm) are laboratory packed with approximately 650 g and 120 g of freshly activated silica gel (grade 923, 100-200 mesh, 60 A°), respectively. The main column is found to stay usable for a year or more based upon the number of separations performed. The polars column not only adsorbs polars but also acts as a guard column and is, therefore, replaced each time a separation is performed.

A commercially prepared silver-loaded silica gel-based-sulfonic acid ($Ag^+$/$SCX^-$-silica gel-Strong Cation Exchange) column (250×21 mm) is used to isolate sulfides. The $Ag^+$/$SCX^-$-silica gel column (250×21 mm) is purchased from Phenomenex. This silver-loaded-strong-cation-exchange column not only holds sulfides and nitrogen compounds, it slows the elution of aromatics significantly and hence results in superior separation between saturates and aromatics. This column is very rugged and reusable for many separations. The use of silver-ion-loaded strong cation exchange ($Ag^+$/$SCX^-$) column has provided a baseline separation between the 'saturates' and the 'aromatics'.

Operational Steps for SGS-HPLC

An instrument method, which controls all the switching valves and the fraction collection valve, was created in such a way that the main column is regenerated at the end of the separation run.

At the system start up, the solvent delivery system is programmed to run cyclohexane at a flow rate of 20 mL/min through all the three columns (see step I of FIG. 1). After about 30-60 min, once the system is stabilized, a 40-60 ml cyclohexane solution of ~3 g DAO sample is injected. Due to the reduced absorbent pore accessibility for the larger DAO molecules and reduced solubility of DAO molecules in the non-polar solvent (used for sample introduction), it was necessary to optimize the sample loading amount. The acceptable loading for a DAO for an optimum fractionation was found to be ~3 grams. When the sample solution is injected, the separation method gets activated. During step I of FIG. 1, the total effluent after passing through the three columns is passed through the UV and RI detectors and then to the fraction collector. This arrangement allows saturates to be separated and eluted. During this step after the saturates are eluted, the pump is switched to run toluene (100%) which will allow aromatics to be eluted out and the polars and sulfides to be retained by the polars and sulfides column, respectively. In steps II and III (FIG. 1), the polars and sulfides columns are back-flushed individually to recover polars and sulfides. Sulfides are back-flushed using 4% and 20% methanol in toluene, whereas polars are recovered using 100% methanol.

Upon completion of a separation run, the system continues running for an additional 50 minutes to regenerate the main column and the sulfides column. The pump method stops the solvent flow and turn off the UV detector at completion of the run. The system is re-flushed/re-generated using additional 100% cyclohexane after a new polars/guard column is installed just before the next sample fractionation.

In addition to collecting saturates, aromatics, sulfides and polars fractions, six additional cuts in-between saturates and aromatics fractions are made and collected in beakers (each one from B-1 to B-5 beakers contain 120 mL, whereas B-6 beaker-contains 220 mL) to establish an acceptable cut-point between saturates and aromatics. Based upon these cuts weight distribution, their UV response, and levels of monoaromatics contamination as determined by $^1$H NMR, the cut-point is moved between beakers, mostly between B-1 to B-3.

The complete solvent evaporation from the resulting fractions, which is done at room temperature using dry nitrogen flow to avoid oxidation, takes about 6-7 days. When the solvent evaporation is near completion, the fractions are transferred to glass vials to determine mass recoveries.

EXAMPLES

Example 1

The eluting-solvent polarity and eluting times for the SGS-HPLC separations procedure were optimized using four DAOs from different crude vacuum resids with the following wt % of nitrogen, sulfur, CCR, MCR, and asphaltenes contents.

|  | Sample A | Sample B | Sample C | Sample D |
|---|---|---|---|---|
| Nitrogen | 0.4 | 0.4 | 1.4 | 0.6 |
| Sulfur | 0.4 | 1.3 | 2.0 | 5.6 |
| Asphaltenes | 16.4 | 4.4 | 12.0 | 35.8 |
| CCR | 7.5 | 9.7 | 16.7 | 29.2 |
| MCR | 8.8 | 11.0 | 20.4 | 28.0 |

These DAOs were selected because, they cover wide ranges of N (0.4-1.4%), S (0.4-5.6%), CCR (7.5-29.2%), MCR (8.8-28%), and Asphaltenes (4.4-35.8%) contents.

Final HPLC separation conditions were set as shown in Table 1.

TABLE 1

SGS Fraction Eluting and Column Regeneration Program

| Elution Step | Time (min) | Cyclo-Hexane % | Toluene % | Methanol % | Flow mL/min | Solvent Mixing Curve |
|---|---|---|---|---|---|---|
| Eluting Saturates | Initial | 100.0 | 0.0 | 0.0 | 20.00 | |
| | 40.00 | 100.0 | 0.0 | 0.0 | 20.00 | |
| Eluting Saturates, Aromatics and Moving Sulfides to Ag+/SCX− Column | 40.00 | 0.0 | 100.0 | 0.0 | 20.00 | 11 |
| | 175.00 | 0.0 | 100.0 | 0.0 | 20.00 | |
| Eluting Sulfides 1 by back-flushing | 175.00 | 0.0 | 96.0 | 4.0 | 20.00 | 11 |
| | 200.00 | 0.0 | 96.0 | 4.0 | 30.00 | |
| Eluting Sulfides-2 by back-flushing | 200.00 | 0.0 | 50.0 | 50.0 | 30.00 | 11 |
| | 210.00 | 0.0 | 0.0 | 100.0 | 30.00 | 11 |
| | 218.00 | 0.0 | 100.0 | 0.0 | 30.00 | 11 |
| Eluting Polars by back-flushing | 232.00 | 0.0 | 0.0 | 100.0 | 30.00 | 11 |
| | 262.00 | 0.0 | 100.0 | 0.0 | 30.00 | 11 |
| Re-generating Main and Sulfides Columns | 282.00 | 100.0 | 0.0 | 0.0 | 30.00 | 11 |
| | 360.00 | 100.0 | 0.0 | 0.0 | 0.00 | 11 |

The collection volumes (mL) for the various cuts, which could be adjusted/optimized as needed in the HPLC procedure, are provided in Table 2

TABLE 2

| Saturates | B-1 | B-2 | B-3 | B-4 | B-5 | B-6 | Aromatics | Sulfides1 | Sulfides2 | Polars |
|---|---|---|---|---|---|---|---|---|---|---|
| 520 | 120 | 120 | 120 | 120 | 120 | 220 | 1940 | 510 | 870 | 1500 |

Although saturates are eluted with cyclohexane, any other low boiling solvent, e.g. n-heptane can be used. Similarly, the aromatics, polars, and sulfides can also be eluted with any pure and/or combinations of organic solvents other than mentioned in Table 1.

Based upon the materials weight distribution trend and their UV detector response, the materials in beakers B-1 to B-6, are combined with saturates and the aromatics, mostly the B-1 & B-2 materials with saturates, and B-3 to B-6 with aromatics. Material weights in beakers for the four DAOs separations are given below in Table 3.

TABLE 3

Cuts In-between Saturates and Aromatics Fractions

| | B-1 mg | B-2 mg | B-3 mg | B-4 mg | B-5 mg | B-6 mg |
|---|---|---|---|---|---|---|
| Sample A | 454 | 60 | 28 | 24 | 298 | 266 |
| Sample B | 105 | 52 | 28 | 25 | 228 | 374 |
| Sample C | 21 | 15 | 9 | 9 | 338 | 288 |
| Sample D | 61 | 30 | 19 | 18 | 686 | 347 |

The normalized wt % data for the separated fractions and the actual total mass recovery for the four DAOs provided by the SGS-HPLC separations are shown in Table 4.

TABLE 4

SGS data for 4 different DAOs

| | Sample A | Sample B | Sample C | Sample D |
|---|---|---|---|---|
| Saturates | 54.7 | 29.5 | 7.8 | 14.1 |
| Aromatics, | 35.6 | 54.6 | 54.4 | 64.3 |
| Sulfides | 5.9 | 9.8 | 20.1 | 13.8 |
| Polars | 4.0 | 6.1 | 17.7 | 7.8 |
| Total Mass Recovery | 100.2 | 103.8 | 97.7 | 100.9 |

As shown above in Table 4, the total mass recoveries in all four separations are excellent and are close to 100% within experimental/method error. Based upon the proton NMR, saturates are found to be contaminated by 4-11% Alkylated-mono-aromatics. The level of aromatic contamination in saturates is found to depend upon the amount and the type of mono-aromatic molecules present in a DAO. The larger the amount of aromatics, the higher is the contamination.

Example 2

Once the technique was optimized, four DAOs were prepared from a set of compositionally diverse 4 vacuum resids were selected to further test the separation procedure. The resids were de-asphalted using n-heptane. One of resids was found to contain almost zero amount of asphaltenes.

The 4 DAOs were separated using the SGS-HPLC technique. The SGS separation results are provided in the data Table 5. As shown by the separation data, the distributions of three fractions, namely saturates, aromatics, and sulfides for the four DAOs are very different, whereas the polars remained almost same. We also found that the sulfides' mass recoveries follow (qualitatively) with total S and N contents. Two of the four DAOs (one of them is highly paraffinic) gave low total mass recoveries. The exact cause for low recoveries is unknown at this time.

TABLE 5

Silica Gel Separation Data for Four Compositionally Diverse DAOs

| | Wt %, (Normalized for fractions) | | | | |
|---|---|---|---|---|---|
| | Saturates | Aromatics | Sulfides | Polars | Actual Total Recovery |
| Sample E | 13.3 | 64.6 | 18.1 | 4.0 | 99.3 |
| Sample F | 6.0 | 52.6 | 36.3 | 5.1 | 98.5 |
| Sample G | 7.7 | 58.6 | 26.9 | 6.8 | 82.6 |
| Sample H | 41.1 | 44.7 | 10.8 | 3.5 | 87.7 |

II. Low Temperature Aromatic Ring Class HPLC Separation Technique

A sub-ambient charge transfer preparative HPLC technique has been developed to fractionate DAO aromatics into aromatic ring classes (ARCs) compounds. In a typical ARC separation, about 200 mg of DAO aromatics are fractionated into one-, two-, three-, and four+ rings fractions. Proton NMR was used to evaluate the effects of changing solvent polarity on cut points during separation optimization. The proton NMR is most effective for determining the cut point between ARC-1 and ARC 2 fractions.

The ARC HPLC system (shown below) consisted of a Waters quaternary solvent delivery systems (W600), a manual 2 ml sample loop injector, a 10-position electrically actuated valve (Valco Model ECSD10P), a Valco backflushing valve (EC6V), and a Waters photodiode-array detector (Model PDA-991). A column (500 mm×25 mm I.D.) packed with 10 micron particles of [3-(2,4-dinitroanilino-)-Propyl]-silica (DNAP-silica or DNAP) was supplied by ES Industries (Marlton, N.J.). The column always remains completely immersed in a continuous flow of methanol maintained at −40±1° C. with a constant temperature refrigerated re-circulating bath (Neslab Model LT-50DD). The commercially available HPLC grade mobile phases, n-pentane and methylene chloride, were used after overnight drying over freshly activated 4 A molecular sieves (8-12 mesh, purchased from Aldrich Chemical Company) at 180° C. under vacuum for about 24 hrs. Dry solvents were required to prevent column plugging. A photodiode-array detector (PDA-991) was utilized to measure the spectra in the range of 190-400 nm at intervals of 1.3 nm every 25 sec over a period of 600 min. A 1-mm path length cell was used for the UV/Vis measurements.

Operational Logic of ARC-HPLC System

In a typical run, the initial mobile phase (100% n-pentane) was passed through the HPLC system for about 60 min at a flow rate of 8.0 ml/min in order to ensure that the sample loop, the column, the detector cell and the valves are thoroughly cleaned and equilibrated with n-pentane.

After the HPLC system reached a steady state which was shown by smooth baselines on two selected wavelengths (nm): 260, and 225 at the UV detecetor. A run was started by switching the sample valve to "Inject" position. The ARC-1, ARC-? ARC-2, ARC-3, and ARC-4+, fractions were separated by changing the eluted solvent polarity. The separated fractions were collected in four one-liter and a 500-ml Erlenmeyer flasks over a period of 650 minutes according to the separation solvent program. The ARC-? fraction was combined with either ARC-1 or ARC-2 fraction depending upon the proton NMR analysis. The eluting solvent was evaporated with the help of nitrogen. On completion of a run, the HPLC system was automatically regenerated by flushing with 1000 ml of n-pentane.

An ARC separation of an aromatics sample takes about 650 minutes from start to completion. Once the run is started, the HPLC system runs unattended and stops at the completion of the separation. The complete solvent evaporation from the resulting fractions, which is done at room temperature using nitrogen to avoid oxidation, takes only one day. When the solvent evaporation is near completion, the fractions are transferred into 20 ml glass vials to determine wt % mass recoveries.

EXAMPLES

Example 1

ARC Separation Method Optimization

Once the SGS technique was optimized, the low temperature ARC separation system was tested to see if 100% of DAO aromatics can be eluted at sub-ambient temperature of −40° C. At the very first attempt, it was observed that the DAO aromatics would not dissolve in n-heptane, a non-polar solvent. Also, the next common non-polar solvent, cyclohexane, used in most liquid chromatographic separations, could not be used at −40° because of its relatively high freezing point (4° C.). Therefore, it was decided to use toluene—a relatively less polar and a good dissolving solvent which could be used at sub-ambient temperatures. It was then optimized the eluting solvent/solvent-mixture volume and polarity in order to recover all of the aromatics. Given FIG. 3 are the ARC separation chromatograms of aromatics of the four DAOs used during optimizing the HPLC separation techniques.

It was observed that the ARC separations for the four DAO aromatics are very similar (shown by ARC-HPLC chromatograms) and the total mass recoveries were 99±3 Wt %. Since the four separation chromatograms were similar, the ARC technique was optimized using Sample D aromatics.

The overlap between the ARC fractions, particularly between ARC-1 and ARC-2, was minimized, as guided by the $^1$H NMR, by adjusting the solvent polarity with varying the methylene chloride percentage in n-pentane.

The column loading capacity was also optimized. To minimize the overlap between the various ARC classes of compounds, the loading amount was reduced to a minimum acceptable amount of 200 mg. The final fraction eluting solvent program is given in Table 6.

TABLE 6

ARC Fraction Eluting and Column Regeneration Program
(In parentheses are the fraction collection times in minutes)

| Elution Step | Time (min) | Pentane % | Methylene Chloride % | Flow mL/min | Solvent Mixing Curve |
|---|---|---|---|---|---|
| Eluting ARC-1 | Initial | 100.0 | 0.0 | 8.00 | |
| (10-95) | 80.00 | 100.0 | 0.0 | 8.00 | |
| Eluting ARC-? | 80.00 | 99.0 | 1.0 | 8.00 | 6 |
| (95-130) | 110.00 | 96.0 | 4.0 | 8.00 | 11 |
| Eluting ARC-2 | 110.00 | 96.0 | 4.0 | 8.00 | |
| (130-300) | 280.00 | 96.0 | 4.0 | 8.00 | |
| Eluting ARC-3 | 310.00 | 80.0 | 20.0 | 8.00 | 6 |
| (300-450) | 450.00 | 80.0 | 20.0 | 8.00 | |
| Eluting ARC-4+ | 450.00 | 0.0 | 100.0 | 5.00 | 11 |
| (450-650), BF mode | 550.00 | 0.0 | 100.0 | 5.00 | |
| System Cleaning | 550.00 | 100.0 | 0.0 | 5.00 | 11 |
| and | 600.00 | 100.0 | 0.0 | 5.00 | |
| Regeneration | 650.00 | 100.0 | 0.0 | 0.00 | |

Example 2

Once the ARC technique was optimized, the four aromatic fractions (from the SGS) of compositionally diverse DAOs (Samples E to H—see Table 5) were further fractionated in to ARC-1, ARC-2, ARC-3, and ARC-4+ fractions. The ARC separation data is given in the data Table 7. As shown by the data, there are large variations in ARC-1 and ARC-4+ fractions for the four aromatic fractions. However, there are relatively low variations in ARC-2 and ARC-3 fractions. Variations in total mass recoveries were also greater than that of experimental/method errors.

TABLE 7

Mass Recovery Aromatic Ring Class Separation Data for four compositionally Different DAOs' Aromatics

| | Wt % (Normalized for Fractions) | | | | |
|---|---|---|---|---|---|
| | ARC-1 | ARC-2 | ARC-3 | ARC-4+ | Actual Total Recovery |
| Sample E | 2.3 | 10.3 | 26.5 | 50.6 | 89.6 |
| Sample F | 5.9 | 13.2 | 26.9 | 49.4 | 95.3 |
| Sample G | 14.2 | 14.6 | 32.3 | 41.1 | 102.2 |
| Sample H | 14.4 | 16.2 | 30.1 | 32.9 | 93.7 |

BACKGROUND REFERENCES

1. L. R. Snyder; *Anal. Chem.*, 36, 774, 1964.
2. J. C. Suatoni and R. E. Swab; *J. Chromatographic Science*, 14, 535, 1976.
3. K. H. Altgelt and M. M. Boduszynski in *Composition and Analysis of Heavy Petroleum Fractions*, Mercel Dekker, Inc., New York, 1994, pp 241-255 and the references cited therein.
4. E. Lundanes and T. Greibrokk; *J. Liquid Chromatography*, 8 (6), 1035, 1995
5. L. Marbognani and A. Izquierdo; *Fuel. Sci. Tech. Int.*, 8(1), 1, 1990.
6. M. F. M. Guadalupe, V. A. Castello Branco and J. C. Schmid; *Org. Geochem*, 17(3), 355, 1991.
7. W. L. Orr: *Anal. Chem.*, 38 (11), 1558, 1966.
8. W. E. Haines and C. J. Thompson, *United States Energy Research & Development Administration, publication*, LERC/RI-75-5 and BERC/RI-75/2, July 1975.
9. P. C. Hayes and S. D. Anderson; *J. Chromatographic Sci.*, 26, 210, 1988.
10. F. P. DiSanzo, S. P. Herron, B. Chawla and D. Halloway; *Anal. Chem.*, 65, 3359, 1993.

What is claimed is:

1. A method for the chromatographic separation of a de-asphalted oil (DAO) extracted from a petroleum vacuum resid boiling above 1000° F., comprising:
   a) passing a mixture of the de-asphalted oil (DAO) through a preparative high performance liquid chromatographic separation in columns including a polars column to separate polars; a main column to separate saturates from aromatics; and a sulfides column to separate sulfides to separate the DAO into saturates, aromatics, sulfides, and polars and collecting the separated saturates, aromatics, sulfides, and polars fractions; and
   b. passing said aromatics fraction through a preparative high performance liquid chromatographic [3-(2,4-dinitroanilino-) propyl]-silica gel (DNAP-silica) column at sub-ambient temperature below 0° C. to fractionate the aromatics into different Classes based upon aromatic ring size and
   collecting separated 1-Ring, 2-Ring, 3-Ring and 4+Ring-4 aromatic fractions.

2. The method of claim 1 wherein the separated aromatic ring classes are composed of aromatic hydrocarbons plus thiophenic compounds.

3. The method of claim 1 wherein said sulfides column of setp a) includes a silver nitrate strong-cation-exchange ($Ag^+$/$SCX^-$-silica gel) column.

4. The method of claim 1 wherein said polars column and said main column include silica-gel columns.

5. The method of claim 1 wherein vacuum resid de-asphalted oil (DAO) has a sample size between about 2 grams and 4 grams.

6. The method of claim 1 wherein said sample to silica gel has a ratio of 1:250.

7. The method of claim 1 wherein the saturates are eluted after the sample passes through the three sections of step a).

8. The method of claim 7 wherein the aromatics are eluted after the saturates are eluted and the polars and sulfides are retained by the polars and sulfide columns, respectively.

9. The method of claim 8 wherein the polars and sulfides are backflushed to recover polars and sulfides after the aromatics are eluted.

10. The method of claim 1 wherein the temperature at which the aromatics are separated in the (DNAP-silica) column is about −40° C.

11. The method of claim 1 wherein the aromatics fraction separated in step a) has a sample amount of less than 300 mg.

* * * * *